United States Patent
Bilgic

(10) Patent No.: US 9,849,255 B2
(45) Date of Patent: Dec. 26, 2017

(54) INHALATION DEVICE

(71) Applicant: Mahmut Bilgic, Istanbul (TR)

(72) Inventor: Mahmut Bilgic, Istanbul (TR)

( * ) Notice: Subject to any disclaimer, the term of this patent is extended or adjusted under 35 U.S.C. 154(b) by 588 days.

(21) Appl. No.: 14/360,014

(22) PCT Filed: Nov. 26, 2012

(86) PCT No.: PCT/TR2012/000200
§ 371 (c)(1),
(2) Date: May 22, 2014

(87) PCT Pub. No.: WO2013/095311
PCT Pub. Date: Jun. 27, 2013

(65) Prior Publication Data
US 2014/0318538 A1 Oct. 30, 2014

(30) Foreign Application Priority Data
Nov. 25, 2011 (TR) ................. 2011 11671

(51) Int. Cl.
*A61M 15/00* (2006.01)
*A61M 11/00* (2006.01)

(52) U.S. Cl.
CPC ...... *A61M 15/0035* (2014.02); *A61M 11/003* (2014.02); *A61M 15/0021* (2014.02); *A61M 15/0026* (2014.02); *A61M 15/0028* (2013.01); *A61M 15/0041* (2014.02); *A61M 15/0081* (2014.02); *A61M 2202/064* (2013.01); *A61M 2205/276* (2013.01)

(58) Field of Classification Search
None
See application file for complete search history.

(56) References Cited

U.S. PATENT DOCUMENTS

| | | | | |
|---|---|---|---|---|
| 5,113,855 A | * | 5/1992 | Newhouse | A61M 15/0091 128/203.12 |
| 5,619,984 A | | 4/1997 | Hodson et al. | |
| 5,657,749 A | | 8/1997 | Cox | |
| 6,092,522 A | | 7/2000 | Calvert et al. | |
| 6,234,365 B1 | | 5/2001 | Bougamont et al. | |
| 6,880,555 B1 | | 4/2005 | Brunnberg et al. | |
| 7,694,676 B2 | * | 4/2010 | Wachtel | A61M 15/0028 128/203.15 |
| 2002/0132001 A1 | | 9/2002 | Garthwaite et al. | |
| 2003/0172927 A1 | * | 9/2003 | Young | A61M 15/0045 128/203.15 |
| 2004/0094152 A1 | | 5/2004 | Harvey et al. | |

(Continued)

FOREIGN PATENT DOCUMENTS

| | | |
|---|---|---|
| CA | 2544745 A1 | 5/2005 |
| EP | 1175220 B1 | 4/2005 |

(Continued)

OTHER PUBLICATIONS

International Search Report and Written Opinion for PCT/TR2012/000200, dated Jun. 10, 2013 (10 pages).

*Primary Examiner* — Tan-Uyen T Ho
*Assistant Examiner* — Jonathan Paciorek
(74) *Attorney, Agent, or Firm* — Clark & Elbing LLP

(57) ABSTRACT

The present invention relates to an inhalation device used for inhalation of the medicament in dry powder form from capsules.

15 Claims, 12 Drawing Sheets

(56) References Cited

U.S. PATENT DOCUMENTS

| | | | |
|---|---|---|---|
| 2004/0182387 A1* | 9/2004 | Steiner | A61M 15/0028 128/203.15 |
| 2004/0266869 A1* | 12/2004 | Montague | A61K 9/0073 514/554 |
| 2005/0005934 A1 | 1/2005 | Harvey | |
| 2005/0154491 A1 | 7/2005 | Anderson et al. | |
| 2005/0172964 A1 | 8/2005 | Anderson et al. | |
| 2005/0183723 A1* | 8/2005 | Pinon | A61M 15/0065 128/203.15 |
| 2005/0268909 A1 | 12/2005 | Bonney et al. | |
| 2005/0279357 A1* | 12/2005 | Wachtel | A61K 9/0073 128/203.15 |
| 2006/0196504 A1 | 9/2006 | Augustyn et al. | |
| 2006/0243275 A1* | 11/2006 | Ruckdeschel | A61M 15/0091 128/200.23 |
| 2007/0062525 A1 | 3/2007 | Bonney et al. | |
| 2007/0137645 A1* | 6/2007 | Eason | A61M 15/0028 128/203.15 |
| 2008/0196718 A1 | 8/2008 | Connell et al. | |
| 2008/0308102 A1 | 12/2008 | Davies et al. | |
| 2009/0078252 A1 | 3/2009 | Anderson et al. | |
| 2009/0139516 A1 | 6/2009 | Augustyn et al. | |
| 2009/0165791 A1* | 7/2009 | Wendland | A61M 15/0028 128/203.21 |
| 2009/0188498 A1 | 7/2009 | Thoemmes et al. | |
| 2009/0211576 A1* | 8/2009 | Lehtonen | A61M 15/00 128/203.12 |
| 2010/0000528 A1 | 1/2010 | Palmer et al. | |
| 2010/0000529 A1 | 1/2010 | Prime et al. | |
| 2010/0059052 A1 | 3/2010 | Davies et al. | |
| 2011/0232637 A1* | 9/2011 | Kaemper | A61M 15/0028 128/203.12 |
| 2012/0260917 A1 | 10/2012 | Bilgic | |
| 2014/0318538 A1 | 10/2014 | Bilgic | |

FOREIGN PATENT DOCUMENTS

| | | |
|---|---|---|
| EP | 2082759 A1 | 7/2009 |
| EP | 2082764 A1 | 7/2009 |
| GB | 1459426 A | 12/1976 |
| GB | 2409042 A | 4/2005 |
| GB | 2447560 A | 9/2008 |
| WO | WO-00/33847 A1 | 6/2000 |
| WO | WO-01/41770 A2 | 6/2001 |
| WO | WO-02/36189 A1 | 5/2002 |
| WO | WO-03/095010 A2 | 11/2003 |
| WO | WO-2006/066908 A1 | 6/2006 |
| WO | WO-2007/012960 A1 | 2/2007 |
| WO | WO-2008/074098 A1 | 6/2008 |
| WO | WO-2009/003989 A1 | 1/2009 |
| WO | WO-2009/139731 A1 | 11/2009 |
| WO | WO-2011/133740 A1 | 10/2011 |

\* cited by examiner

INHALATION DEVICE

CROSS-REFERENCE TO RELATED APPLICATIONS

This application is the U.S. National Stage of International Application No. PCT/TR2012/000200, filed Nov. 26, 2012, which claims priority to Turkish Application No. TR2011/11671, filed Nov. 25, 2011.

The present invention relates to an inhalation device used for inhalation of medicaments in dry powder form from capsules. A capsule which is loaded to the capsule chamber of the inhalation device prior to inhalation is pierced by means of at least one needle pushed towards the capsule chamber and the medicament in dry powder form comprised in the capsule becomes ready for inhalation once the patient presses the push button.

Dry powder inhalation devices are the devices used for inhalation of medicaments in dry powder form generally from capsules, blisters or reservoirs. To this respect, dry powder inhalation devices can be either single-dose inhalers or multi-dose inhalers. In order to inhale the medicament in dry powder form from capsules, single-dose dry powder inhalation devices are used while multi-dose inhalation devices are used in order to inhale the medicament in dry powder form from blisters or reservoirs.

The inhalation devices which provide the medicament in dry powder form to be inhaled from capsule are commonly used for inhalation of the medicament in dry powder form. In these inhalation devices, the cover and the mouthpiece are opened generally by the patient rotating them respectively in order to expose the capsule chamber; a capsule is loaded to the capsule chamber and it is pierced by at least one needle moving towards the capsule chamber once an actuation button is pushed or rotated. By this means, the medicament in dry powder form comprised in the pierced capsule becomes ready for inhalation. The inhalation devices described in the patents explained below serve as examples for the inhalation devices having the abovementioned characteristic features.

EP 0703800 (B1) discloses an inhalation device having a bowl-shaped bottom casing, a plate covering this bottom casing and connecting with the capsule chamber, a mouthpiece and a cover protecting the mouthpiece. These components of the device are connected to each other by means of a hinge. In order to place a capsule into the capsule chamber of the inhalation device, primarily the cover is rotated around the hinge until the mouthpiece is exposed; after the mouthpiece is exposed, the mouthpiece is rotated around the hinge until the capsule chamber is exposed. A capsule comprising the medicament in dry powder form is placed into the capsule chamber which appears after the cover and the mouthpiece are rotated individually around the hinge. Then, the mouthpiece is closed over the plate which is connected to the capsule chamber and the capsule in the capsule chamber is pierced when the spring-loaded actuation button on the side-part of the device is pressed and the medicament in dry powder form comprised in the capsule becomes ready for inhalation.

U.S. Pat. No. 7,694,676 (B2) discloses an inhalation device which comprises a bottom casing wherein the capsule chamber is placed, a plate locked to the bottom casing and providing the bottom casing to be closed, a mouthpiece locked to the plate, a cover which hides the mouthpiece in closed position and is locked by means of a closure member. These components are fixed to each other by means of a hinge similar to the device disclosed in the patent above. The actuating button of this device was designed to be double-functional; in the first actuation, the closure member is detached from the bottom casing and the cover becomes rotatable; in the second actuation, the capsule in the capsule chamber is pierced by means of the needles. In the first actuating of the actuation button, the closure member of the cover is released from the bottom casing and the cover can be rotated manually by the patient. After the cover is rotated, the mouthpiece is also removed from the plate by being rotated in order to load the capsule into the capsule chamber. The capsule is loaded to the capsule chamber which is exposed when the mouthpiece is rotated and the mouthpiece is again closed over the plate. In this position, the capsule in the capsule chamber is pierced by the second actuation of the actuating button and the medicament in dry powder form comprised in the capsule becomes ready for inhalation.

The aim of the present invention is to provide the inhalation devices in the prior art to be improved in terms of use which are used for inhalation of the medicament in dry powder form from capsules.

In another aspect, the aim of the present invention is to provide an inhalation device which is easy to use and practical, is prepared in a short time for inhalation of the medicament in dry powder form from capsule. In another aspect, the present invention aims to provide an inhalation device wherein each dose is delivered entirely and accurately, the patients and relatives of the patients can be protected from possible accidents and misuses, and the safe inhalation shall be provided.

According to the present invention, this goal is attained with an inhalation device comprising
- a bottom casing,
- a mid-plate covering the bottom casing,
- a capsule chamber integrated with the mid-plate in order to place the capsule,
- a filter in order to filtrate dry powder formulation,
- a filter connector in order to hold the filter,
- a mouthpiece which is closed over the mid-plate and wherein the filter connector engages,
- an mouthpiece cover in order to cover the mouthpiece,
- a hinge providing the connection between the mouthpiece cover, the mouthpiece, the mid-plate and the bottom casing with each other,
- at least one needle in order to pierce the capsule in the capsule chamber,
- a movable push button in order to push at least one needle into the capsule chamber,
- a safety lock button preventing the movement of the mouthpiece and the mouthpiece cover in sleep mode of the device, characterized in that the safety lock button is connected with both the filter connector inserted into the mouthpiece and the mouthpiece cover, and this connection provides both the mouthpiece and the mouthpiece cover to be released together and simultaneously when the safety lock button is in actuation position for inhalation of the medicament in dry powder form.

The main advantage of the present invention is that before loading a capsule into the capsule chamber, the mouthpiece cover and the mouthpiece are released simultaneously by actuating only the safety lock button without implementing the processes separately in order to move the mouthpiece and the mouthpiece cover and these components become ready to be moved together by the patient. By this way, the processes before loading a capsule into the capsule chamber can be implemented easily and in a short time in order to prepare the inhalation device for use. The fact that the inhalation device becomes ready for use in a short time is of great importance for the patient during asthma attack.

The mouthpiece cover, the mouthpiece, the mid-plate and the bottom casing of the device of the present invention are fixed to each other by a hinge and each of these components can be rotated around the same axis.

Advantageously, thanks to the fact that both the mouthpiece cover and the mouthpiece are released simultaneously by actuating only the safety lock button in the inhalation device of the present invention and they are rotated together by the patient, neither the components required to be comprised in the inhalation device in order to release these two components separately and nor a complicated configuration is needed. Also, this significantly reduces the production cost of the inhalation device. In addition, the devices of the present invention provide safe use since they prevent misuse and they also provide some important advantages in terms of ease of use thanks to this characteristic feature. Furthermore, since the force required for rotating the mouthpiece cover and the mouthpiece which are released by actuating the safety lock button is considerably low, it is not needed for these components to use additional device parts which provide the patient to grip these components tightly. Since the mouthpiece cover and the mouthpiece do not have these parts, the appearance of the inhalation device is improved and these parts are prevented from accumulation of dirt.

In one embodiment of the present invention, the extensions under the mouthpiece cover and the extensions situated on both sides of the filter connector inserted into the mouthpiece insert into the bottom-casing when the inhalation device is closed. Before using the inhalation device, when the safety lock button is in sleep mode, one of the locking latches situated on the safety lock button is interlocked to the hole of an extension under the mouthpiece cover; the other one is interlocked to the hole of an extension belonging to the filter connector. By this way, when the safety lock button is actuated once the patient presses on it, the locking latches situated on the safety lock button are detached from the extensions to which they are interlocked and both the mouthpiece cover and the mouthpiece are released simultaneously. In this position, both the mouthpiece cover and the mouthpiece can be easily rotated together by the patient manually in order to place a capsule into the capsule chamber.

In one preferred embodiment of the present invention, the inhalation device can have one safety lock button located on each of the two sides of the inhalation device which are situated oppositely. The locking latches situated on these safety lock buttons can be interlocked to the holes of the extensions belonging to the mouthpiece and the mouthpiece cover which are located on the same side of the locking latches. In this case, the two safety lock buttons should be actuated simultaneously by being pressed by the patient in order to release the mouthpiece cover and the mouthpiece simultaneously.

In another embodiment of the present invention, there is no need for a spring in order for the safety lock button pushed towards the inside of the bottom casing by the patient to come back to its original position. When the safety lock button is actuated, in other words when the safety lock button is pressed by the patient, its movement towards the bottom-casing and its reverting back to its first position when the safety lock button is released are enabled by the flexible part. When the safety lock button is pressed, this flexible part stretches and it allows the safety lock button to move towards the inside of the bottom-casing and in the case that the press force applied on the safety lock button by the patient is removed, while the flexible part reverts back to its previous position, also the safety lock button reverts back to its previous position.

In another preferred embodiment of the present invention, string-loaded pieces can be placed between the bottom-casing and the mouthpiece and the mouthpiece and/or between the bottom-casing and the mouthpiece cover in order to open the mouthpiece cover and the mouthpiece automatically which are released in actuation position of the safety lock button. In this way, the mouthpiece cover and the mouthpiece are automatically opened and the capsule chamber is exposed once the upper cover and the mouthpiece are released when the safety lock button is in the activation position, without any need for manual opening by the patient. The sizes of these spring parts should be appropriate for providing the automatic opening of the mouthpiece and the mouthpiece cover.

In one embodiment of the present invention, the mouthpiece cover and the mouthpiece released by actuating the safety lock button can be rotated together only up to 90°. The mouthpiece cannot be rotated more than 90°; however the mouthpiece cover can be rotated by 180°. According to this, the mouthpiece and the mouthpiece cover, which move together up to a position of 90°, are separated by the continuing rotation of the mouthpiece cover after said position. Thus, after placing a capsule into the capsule chamber, only the mouthpiece is closed over the bottom casing for inhalation and one of the locking latches on the upper side of the safety lock button is clasped into the hole of the extension belonging to the filter connector engaged to the inside of the mouthpiece, fastening the mouthpiece in this position and thus providing a safe inhalation.

The structure of the hinge unit on the edge of the mouthpiece prevents the mouthpiece from rotating more than 90°. This hinge element has a protruding structure in the manner that it prevents the movement of the mouthpiece more than 90°. After the mouthpiece is rotated by 90°, this protruding part leans on the bottom-casing and it prevents the rotation of the mouthpiece more than 90°.

Synchronized movement of the mouthpiece and the mouthpiece cover is possible with the connection between these two components. This connection is provided in the case that the nails, which are situated on the locations in which the filter connector is interlocked to the mouthpiece, clinch the holes in the interior surface of the mouthpiece cover. Interlocking of the filter connector to the mouthpiece internally is enabled by internally interlocking of the locking latches situated on the filter connector to the holes situated on the sides of the mouthpiece. Fitting of the locking latches on the upper side of the filter connector into the holes on the side-parts of the mouthpiece causes formation of nails on these fitting points on the outer surface of the mouthpiece. By means of clasping of these nails on the outer surface of the mouthpiece into the holes on the inner surface of the mouthpiece cover, these two components synchronize. The mouthpiece cover and the mouthpiece can be rotated together by 90° thanks to this connection between the mouthpiece and the mouthpiece cover. The nails situated on the exterior surface of the mouthpiece are easily detached from the holes situated on the interior surface of the mouthpiece cover as the mouthpiece cover continues to rotate after the mouthpiece stops at this position and the mouthpiece cover and the mouthpiece are separated.

There is an air intake duct passing through the mouthpiece to provide the delivery of the dry powder medicine in the capsule to the patient. One end of this air intake duct reaches to the mouthpiece inlet while the other end is inserted into the filter connector. The point where the air intake duct ends in the filter connector is adjusted in such a way that the dry powder formulation sieved from the filter goes into the air intake duct without dispersing. According to this, the filter connector is connected both to the holes on the side of the mouthpiece and the air intake duct passing through the mouthpiece. The filter which provides to sieve the dry powder medicament comprised in the capsule during inhalation is held by this filter connector. The filter connector, therefore the filter, is in a fixed position due to the connection of the filter connector with said components.

In one preferred embodiment of the present invention, the mid-plate and the capsule chamber are preferably adjacent to each other and the capsule chamber is situated under the mid-plate. By this way, when the mid-plate is rotated away from the bottom-casing in order to clean the inhalation device after inhalation, the capsule chamber is also rotated away from the bottom-casing and the inner side of the bottom-casing can be cleaned easily.

In one embodiment of the present invention, the inhalation device of the present invention comprises a press button which is preferably independent from the safety lock button and actuated when pressed. The press button is preferably situated on the side part of the device and does not outreach the margins of the bottom casing of the device. The needle holder holding the needles piercing the capsule in the capsule chamber is in contact with the press button. The needles held by the needle carrier are placed in the guide rails extending from the side-part of the capsule chamber. Upon pressing the press button, the needle holder moves towards the capsule chamber and the needles pierce the capsule in the capsule chamber moving through the guide rails. In this way, the process of opening the device by the press button which is situated independently from the safety lock button used in order to provide safe inhalation and the process of piercing the capsule are separated. Accidental opening of the capsule due to a user mistake and wasting the dry powder comprised in the capsule are prevented. Advantageously, the needle holder is connected to the mid-plate in the manner that it can easily move towards the capsule chamber and move away from the capsule chamber. A holding member can be situated on a suitable part of the mid-plate which would facilitate holding for the patient. Thanks to this holding member, the mid-plate can be easily rotated.

In another embodiment of the present invention a spring is situated between the capsule chamber and the needle holder in order to revert back the needles to their first position after they pierce the capsule in the capsule chamber. This spring is located on a connecting rod extending from the side-part of the capsule chamber towards the hole in the middle of the needle carrier. In other words, the connection rod appears from the side of the capsule chamber, enters into the hole in the centre of the needle holder by passing through the spring. When the press button is pressed, the needle holder moves towards the capsule chamber, the connection rod moves through the hole in the centre of the needle holder and the spring is compressed. When the press button is released, the spring reverts back to its free position, the needle holder and therefore the needles revert back to their old position.

While using the device, the mouthpiece cover and the mouthpiece which are released simultaneously when the safety lock button is actuated are rotated away from the mid-plate in order to load a capsule into the capsule chamber before inhalation. After the mouthpiece and the mouthpiece cover are rotated together by 90°, the mouthpiece stops at 90° and the mouthpiece cover and the mouthpiece are separated from each other as the mouthpiece cover continues to be rotated. After the capsule is loaded to the capsule chamber, the mouthpiece is again rotated over the mid-plate and the position of the mouthpiece is fixed once the locking latch on the upper part of the safety lock button is clasped into the hole of the extension belonging to the filter connector engaged into the mouthpiece. After the position of the mouthpiece is fixed, the device is actuated pressing on the press button which is preferably situated independent from the safety lock button. The needle holder which is in contact with the press button is pushed towards the capsule chamber as the press button is actuated. While the needle carrier is pushed towards the capsule chamber by the push button to pierce the capsule, the needles carried by the needle carrier proceeds through the guide rails extending towards one side of the capsule chamber and the capsule in the capsule chamber is pierced by these needles. The dry powder formulation comprised in the capsule becomes ready for inhalation.

After inhalation, the mouthpiece is released when the safety lock button is pressed and the empty capsule is removed from the capsule chamber. When required, the device is cleaned by rotating the mid-plate around the hinge.

The components of the device are elucidated below with the drawings and reference numbers without limiting the scope of the invention, only to render the invention more comprehensible.

REFERENCE NUMBERS IN THE FIGURES

Figure 1:
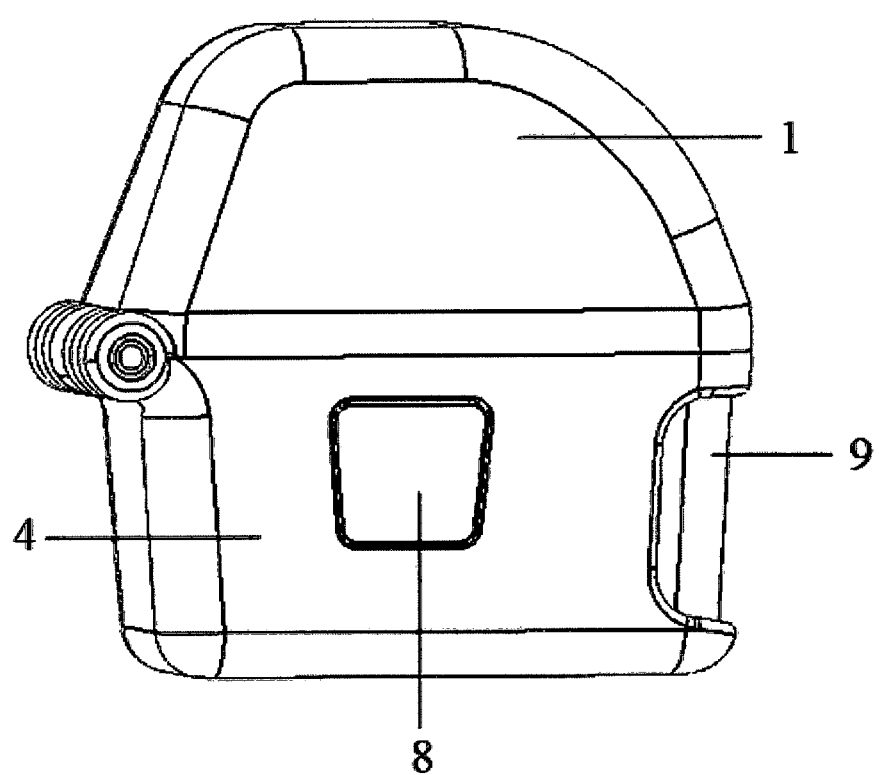
FIG. 1 is a perspective view of the inhalation device in sleep mode.

1 Mouthpiece cover
1a Hinge hole
1b Front extension
1c Back extension
1d Front hole
1e Back hole
2 Mouthpiece
2a Hinge hole 2b First interlocking point
2c Second interlocking point
2d Nail
2e Protruding part
3 Mid-plate
3a Hinge hole
3b Holding member
4 Bottom-casing
5 Air intake duct
6 Filter connector
6a Front locking latch
6b Back locking latch
6c Front extension
6d Back Extension
7 Filter
8 Safety lock button
8a Right locking latch
8b Left locking latch
8c Flexible Part
9 Press button
10 Hinge
11 Capsule chamber
11a Upper guide rail
11b Lower guide rail
11c Connection rod
12 Needle holder
12a Hole
12b Upper needle
12c Lower needle
13 Spring FIG. 1 shows a view of the inhalation device in sleep mode. When the inhalation device is in sleep mode, only the mouthpiece cover (1), the bottom-casing (4), the safety lock button (8) and press button (9) can be seen.

Figure 2:
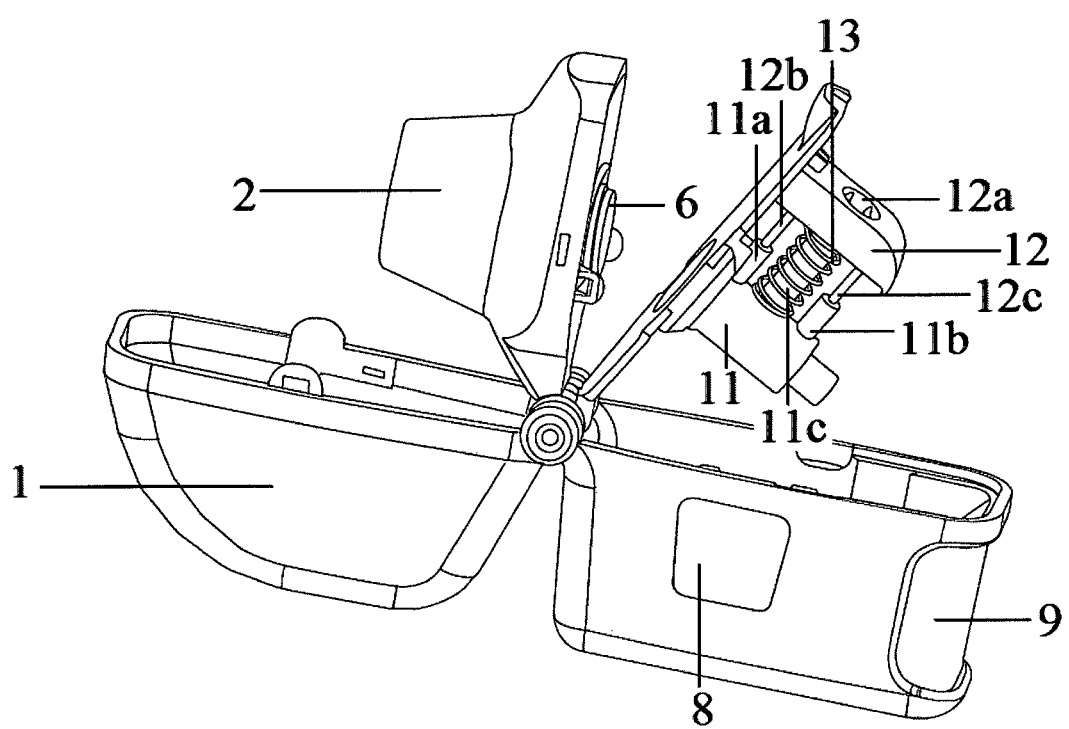
FIG. 2 is a perspective view of the mouthpiece cover, the mouthpiece, the mid-plate and the bottom-casing in disassembled form around the hinge.

The basic components of the device that are the mouthpiece cover (1), the mouthpiece (2), the mid-plate (3) and the bottom-casing (4) are connected to each other by means of a hinge (10) (FIG. 2). Thanks to the connection which is provided by the hinge (10) that goes into the hinge holes (1a, 2a, 3a, 4a) of these components, each component can be rotated easily around the hinge (10).

Figure 3:
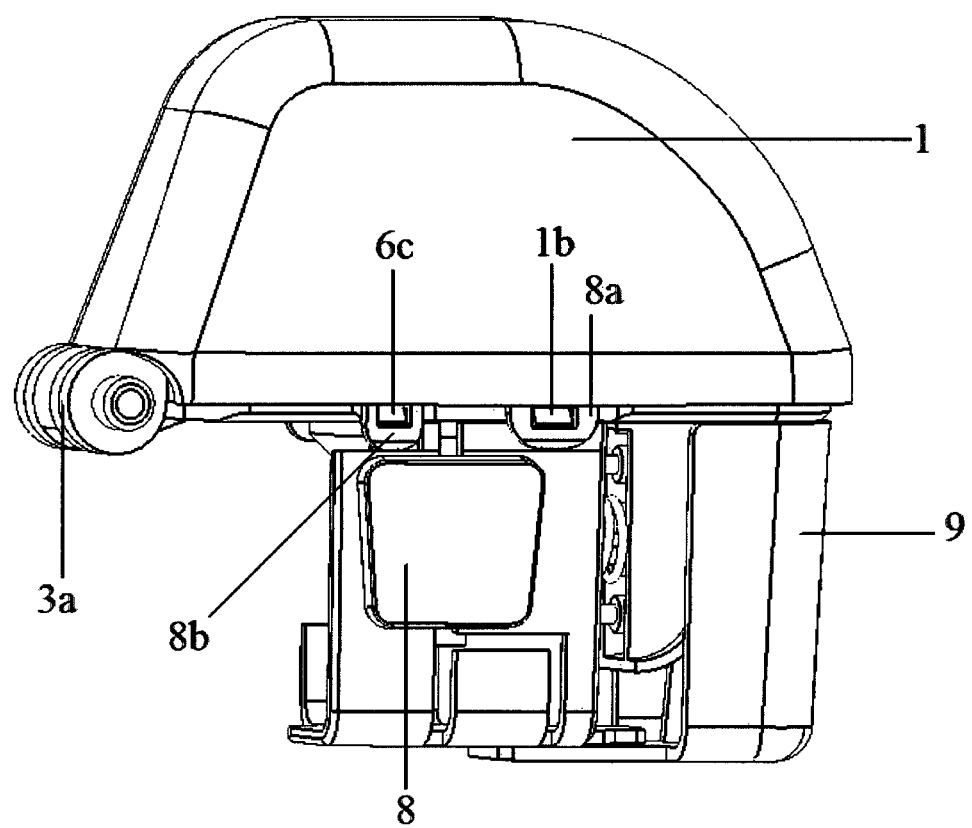
FIG. 3 is a perspective view of the connection of the safety lock button to the mouthpiece cover and the mouthpiece.

When the device is in sleep mode, the safety lock button (8) is also in sleep mode. When both the device and the safety lock button (8) are in sleep mode, the safety lock button (8) is connected to the mouthpiece cover (1) and the mouthpiece (2) in the manner that it prevents the rotation of the mouthpiece cover (1) and the mouthpiece (2) (FIG. 3).

Figure 4A:
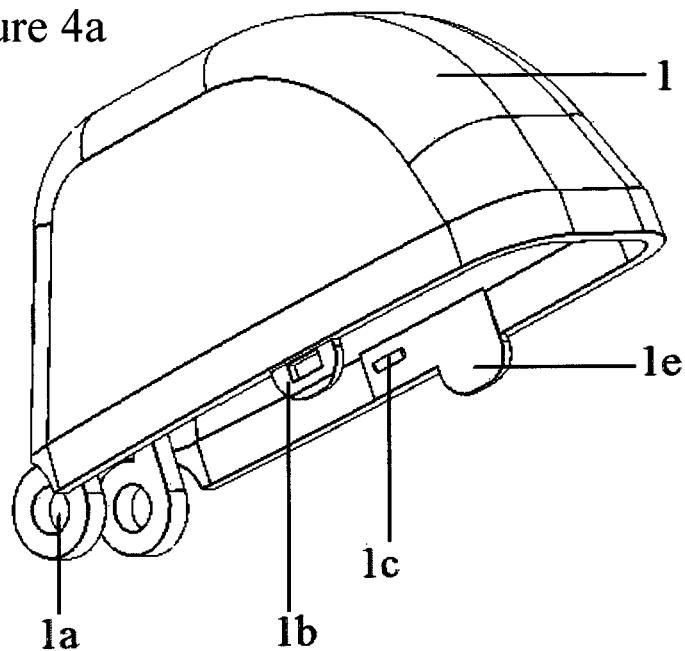
FIG. 4a and FIG. 4b are different perspective views of the mouthpiece cover.
Figure 4B:
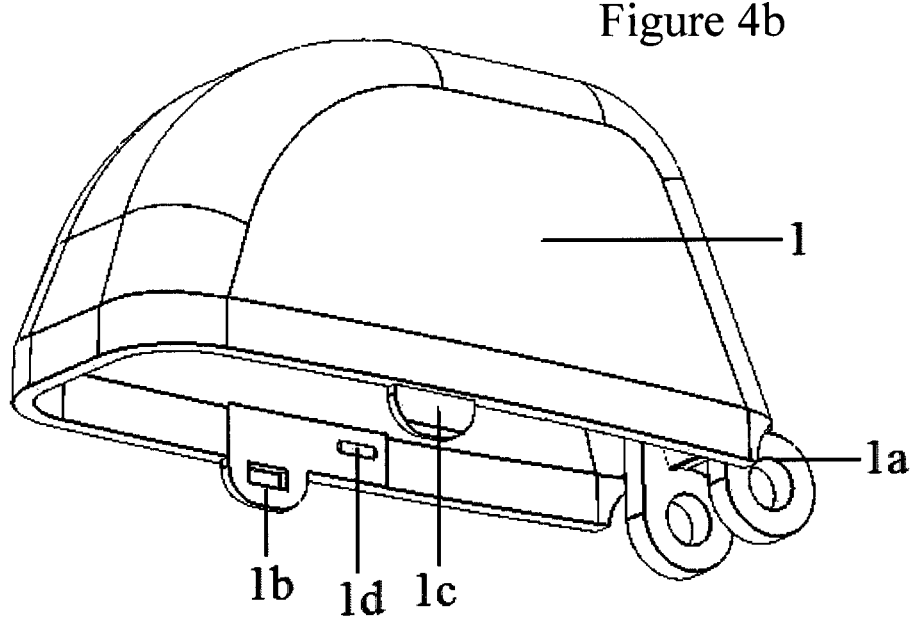
Figure 5A:
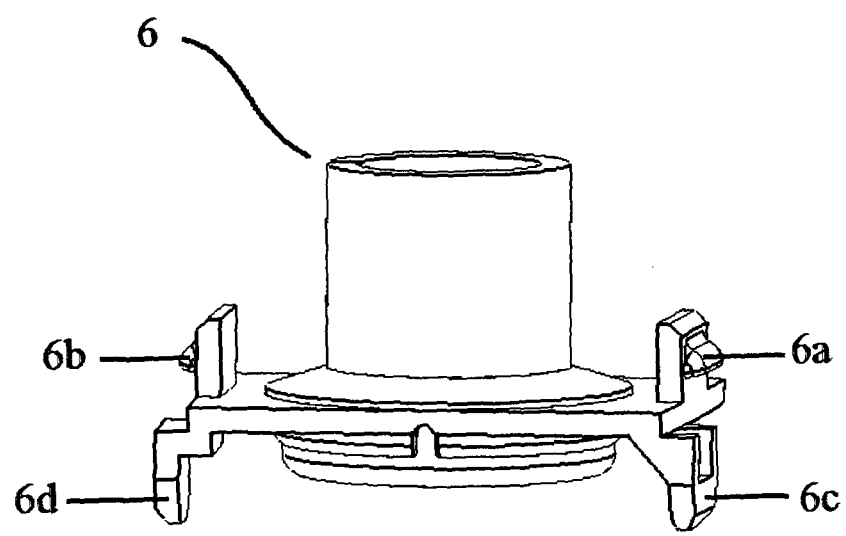
FIG. 5a is a perspective view of the filter connector.
Figure 6A:
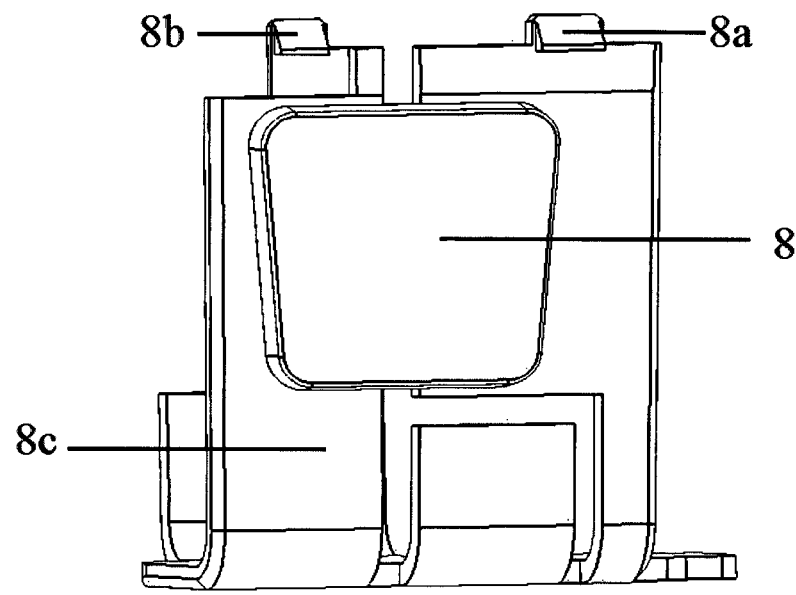
FIG. 6a and FIG. 6b are different perspective views of the safety lock button.
Figure 6B:
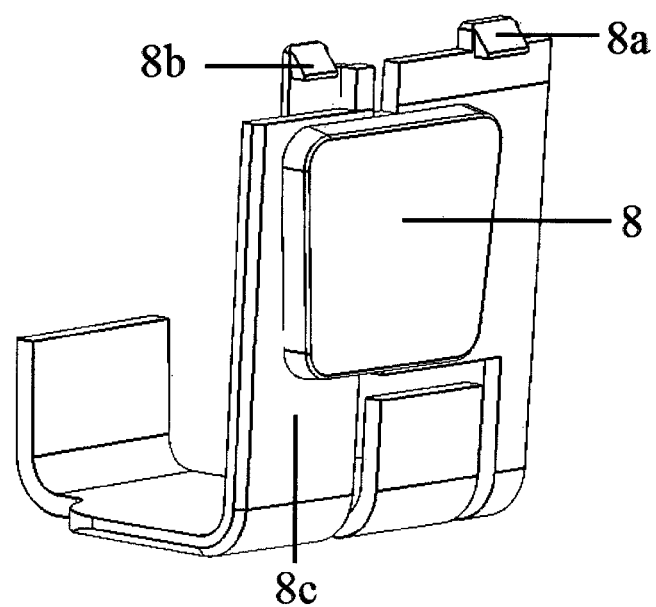

As showed in FIGS. 4a and 4b, there is one extension (1b, 1c) on each side, on front and back sides, under the mouthpiece cover (1). As showed in FIG. 5a, there are extensions on both sides (6c, 6d) of the filter connector (6) inserted the mouthpiece (2). The mouthpiece cover (1) and the mouthpiece (2) are connected to the safety lock button (8) by means of these extensions. The locking latches (8a, 8b) interlocking to these extensions are situated on the safety lock button (8) in order to connect the mouthpiece cover (1) and the mouthpiece (2) to the safety lock button (8) (FIGS. 6a and 6b). The right locking latch (8a) of the locking latches on the safety lock button is interlocked to the hole of the front extension (1b) under the mouthpiece cover, the left locking latch (8b) is interlocked to the hole of the front extension (6c) under the filter connector which is internally interlocked to the mouthpiece (2) (FIG. 3). The other extensions (1c, 6d) of the mouthpiece cover (1) and the filter connector (6) are not perforated since the safety lock button (8) is not interlocked to a locking latch (FIG. 4a, FIG. 4b, FIG. 5a).

Figure 7:
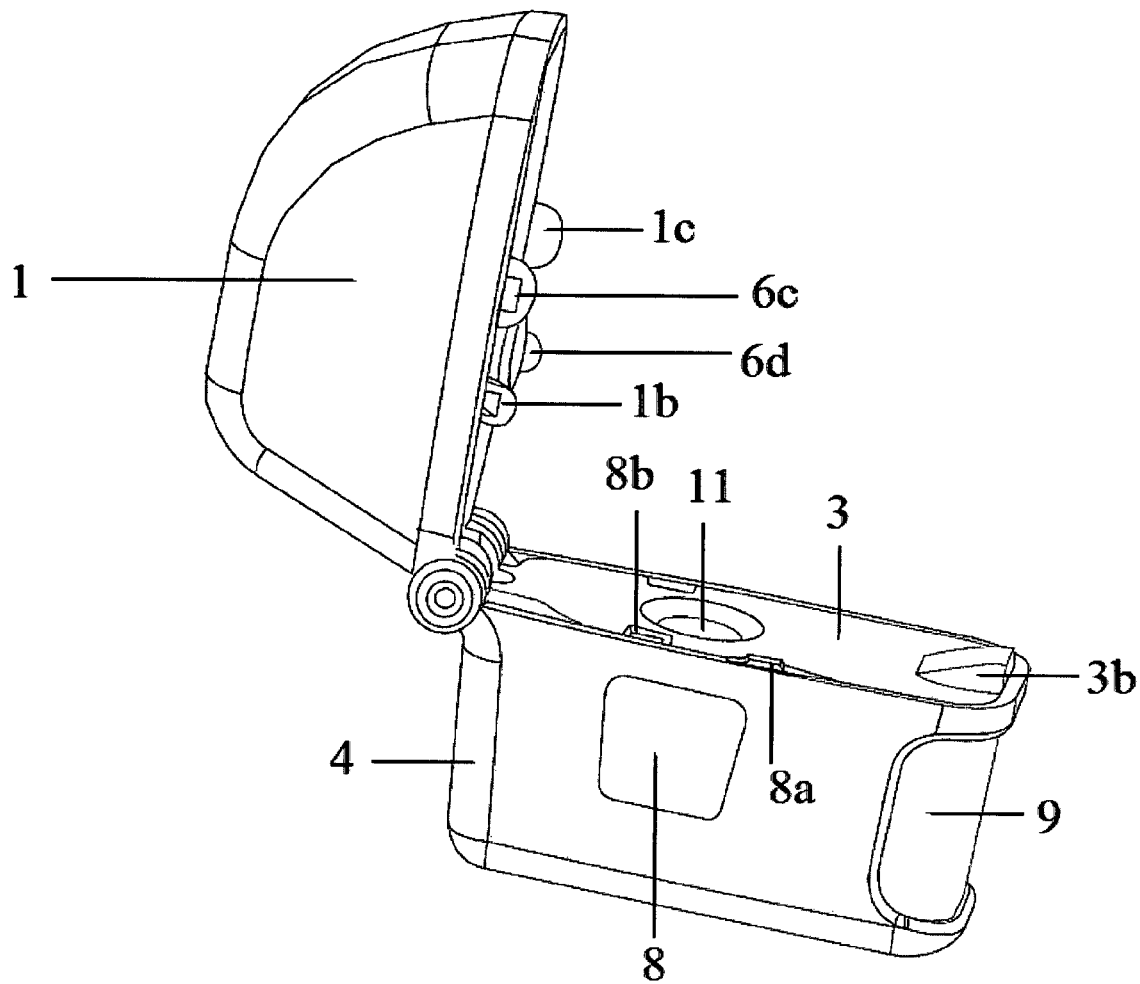
FIG. 7 is a perspective view of the device wherein the synchronized movements of the mouthpiece cover and the mouthpiece is illustrated.

When the safety lock button (8) is pressed by the patient, in other words when a press force is applied on the safety lock button (8) by the patient, the locking latches (8a, 8b) situated on the safety lock button detach from the extensions (1b, 6c) of the filter connector (6) which is internally interlocked to the mouthpiece cover (1) and the mouthpiece. By this way, the mouthpiece cover and the mouthpiece are released simultaneously and rotated together as showed in FIG. 7.

Pressing on the safety lock button (8) to activate it causes the simultaneous release of the mouthpiece cover (1) and the mouthpiece (2) and enables these two components to synchronize. In the case that the safety lock button (8) is released, which moves through the bottom-casing (4) when it is pressed, in other words when the force implemented on the safety lock button (8) by the patient is removed; it reverts back to its first position thanks to the flexible part (8c) in the safety lock button (FIG. 6a and FIG. 6b). The flexible part (8c) stretching when the safety lock button (8) is pressed reverts back to its first position when the safety lock button (8) is released and it causes the safety lock button (8) to revert back to its first position too.

Figure 8:
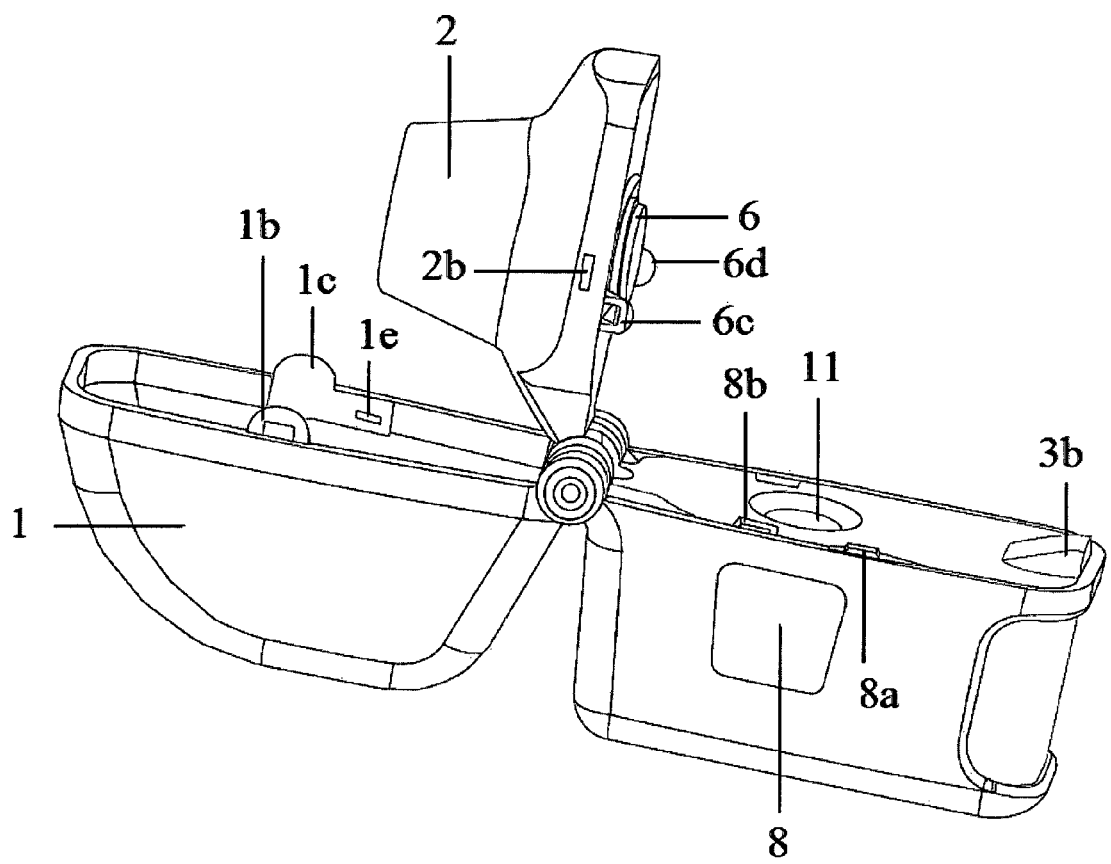
FIG. 8 is a perspective view of the position of the device wherein the mouthpiece cover is illustrated as separated from the mouthpiece.
Figure 10:
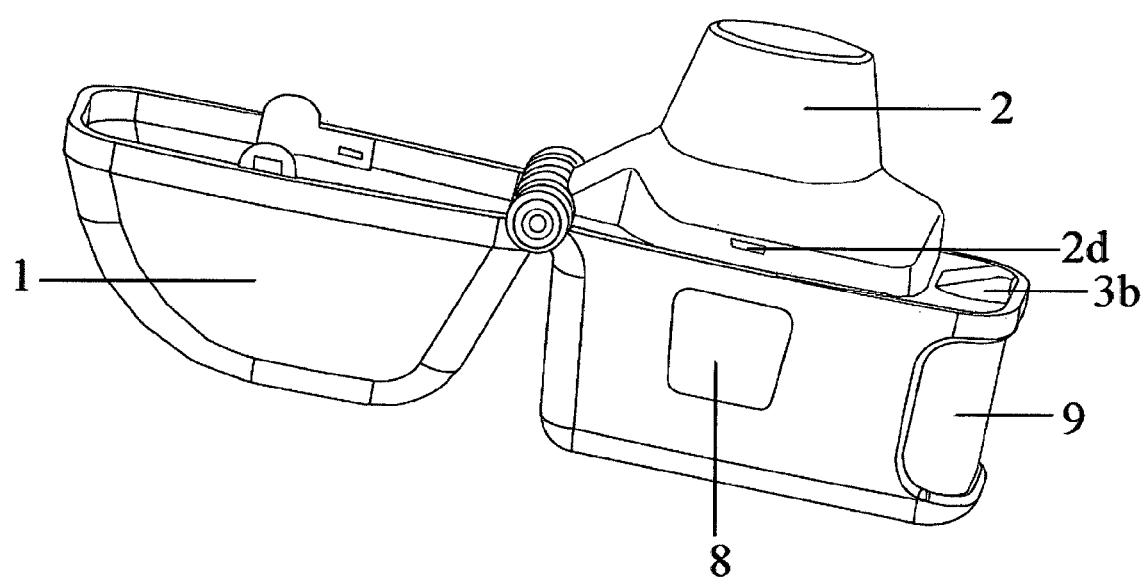
FIG. 10 is a perspective view of the position of the device wherein only the mouthpiece is connected to the safety lock button.

The locking latches (6a, 6b) situated on the filter connector go into the holes on the locking points (2b, 2c) situated on the side of the mouthpiece (2) and provide the filter connector (6) to be interlocked internally to the mouthpiece (2) (FIG. 8). Clasping of the locking latches (6a, 6b) on the upper part of the filter connector into the holes on the interlocking points (2b, 2c) on the sides of the mouthpiece (2) causes formation of nails on these interlocking points (2b, 2c) on the outer surface of the mouthpiece. The nail on the first interlocking point on the side of the mouthpiece goes into the front hole (1d) on the interior surface of the mouthpiece cover; the nail on the second interlocking point on the side of the mouthpiece goes into to the back hole (1e) on the interior surface of the mouthpiece cover. The nail on the first interlocking point is showed in FIG. 10. Thanks to the fact that these nails on the exterior surface of the mouthpiece go into the holes (1d, 1e) on the interior surface of the mouthpiece cover, the mouthpiece cover (1) and the mouthpiece (2) which are released when the safety block button is actuated can be rotated together as showed in FIG. 7.

Figure 9A:
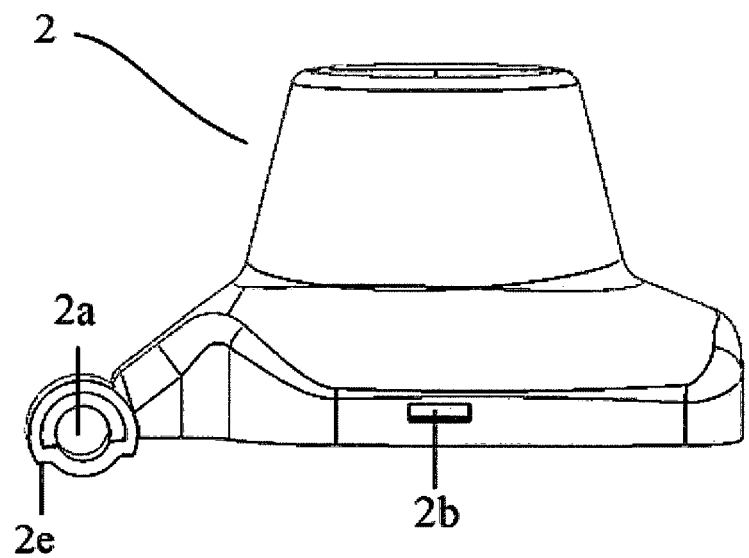
FIG. 9a and FIG. 9b are different perspective views of the mouthpiece.
Figure 9B:
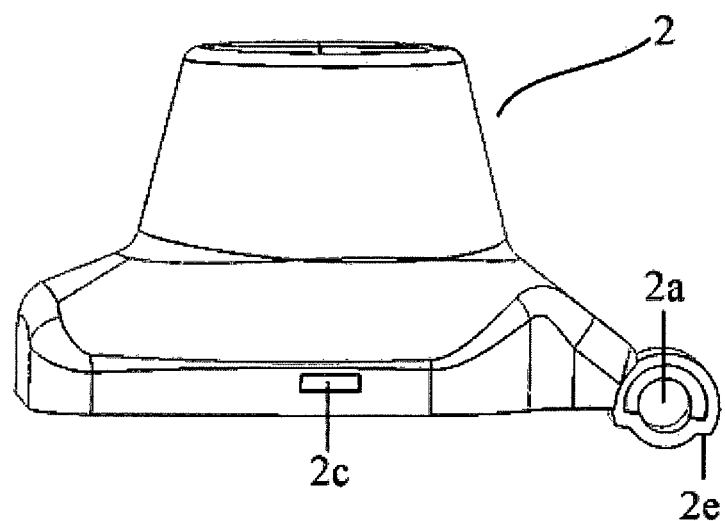

The hinge hole (2a) of the mouthpiece has a protruding structure that does not allow the mouthpiece to be rotated more than 90° (FIG. 8 and FIG. 9). This protruding part (2e) leans on the bottom-casing (4) after the mouthpiece is rotated by 90° and does not allow the mouthpiece (2) to be rotated more than 90°. If the mouthpiece cover (1), which is rotated by 90° together with the mouthpiece (2), is continued to rotate after the mouthpiece (2) stops at 90°, the mouthpiece cover (1) and the mouthpiece (2) are separated from each other as the nails situated on the exterior surface of the mouthpiece (2) detach from the holes (1d, 1e) situated on the internal surface of the mouthpiece cover (1) easily.

While the mouthpiece (2) can be rotated maximum by 90°, the mouthpiece cover (1) can be rotated only by 180°. Thus, the angle between them can be maximum 90° when the mouthpiece cover (1) and the mouthpiece (2) are separated from each other (FIG. 8).

After the mouthpiece cover (1) and the mouthpiece (2), which are released when the safety lock button (8) is actuated, are rotated away from the mid-plate (3) in order to expose the capsule chamber (11), the safety lock button (8) can be released. After a capsule is placed into the capsule chamber (11), the mouthpiece (2) is rotated again over the mid-plate (3) in order to realize inhalation and the mouthpiece is connected to the safety lock button (8) again by interlocking of the left locking latch (8*b*) on the safety lock button (8) to the hole of the front extension (6*c*) under the filter connector and the mouthpiece (2) is fixed for a safe inhalation as showed in FIG. 10.

Figure 11:
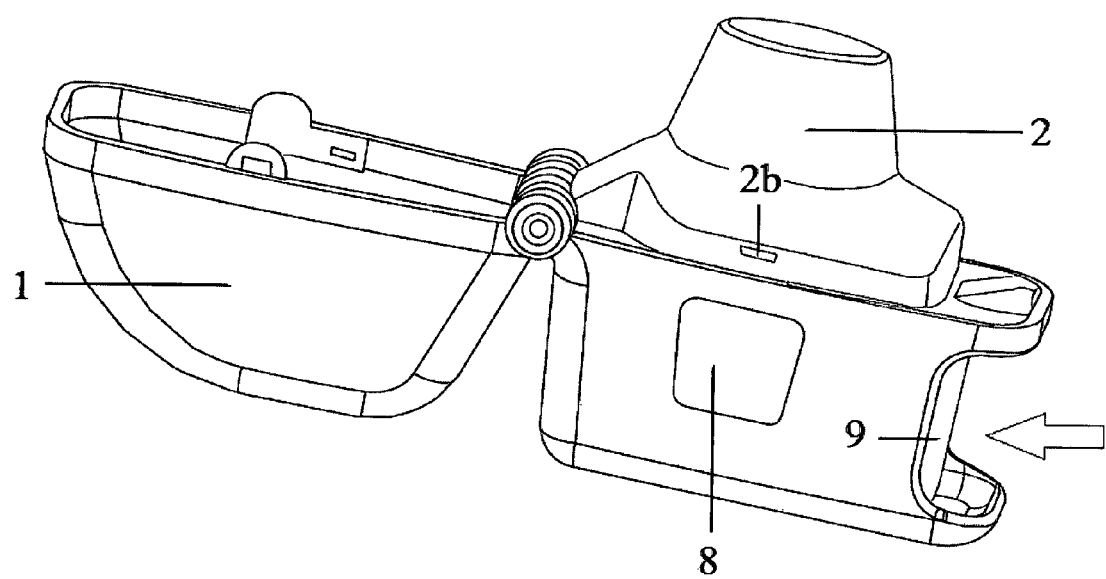
FIG. 11 is a perspective view of the position of the device wherein the press button is pressed.
Figure 12:
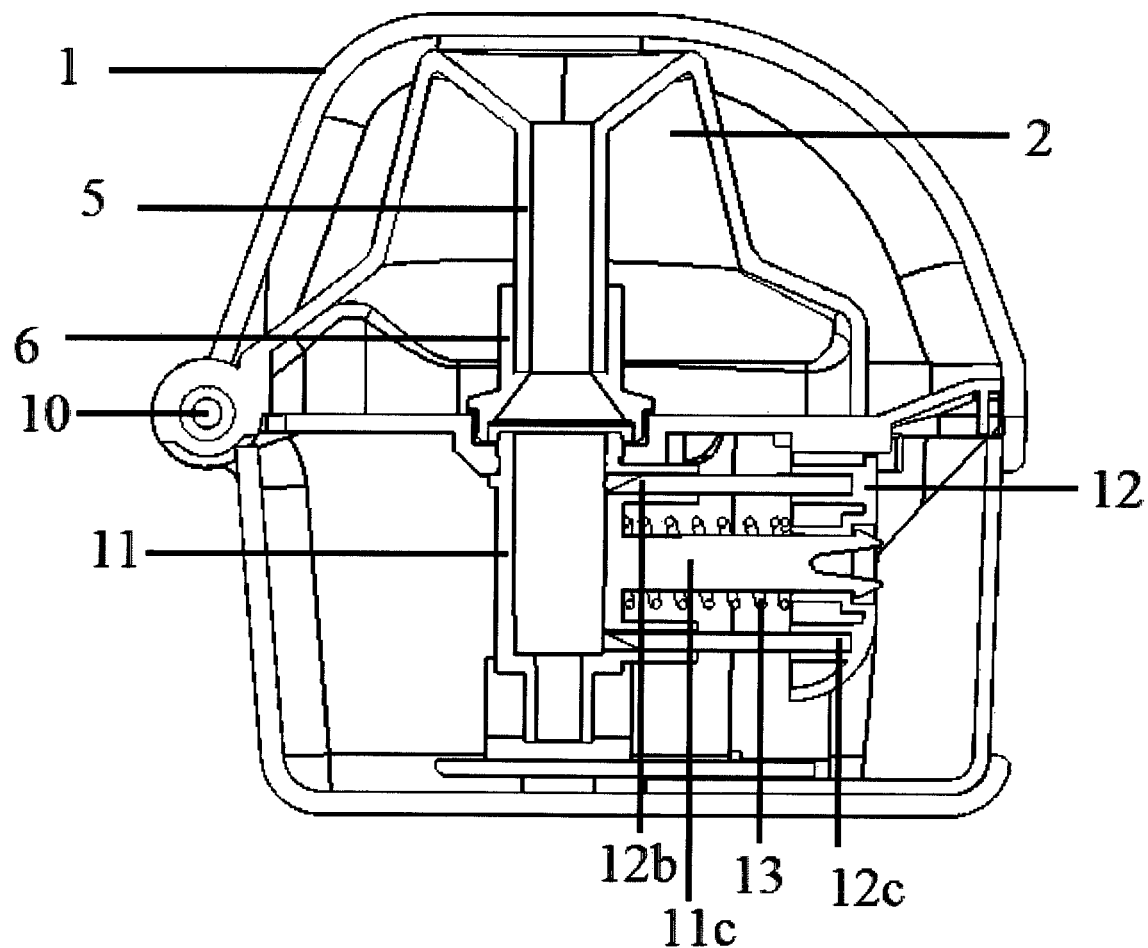
FIG. 12 is a vertical section view of the device.

In order to pierce the capsule in the capsule chamber (11), a press button (9) which is independent from the safety lock button (8) is actuated when the patient presses on it as showed in FIG. 11. When the press button (9) is in sleep mode (FIG. 10), it is in contact with the needle holder (12) holding the needles (12*b*, 12*c*); and the needles (12*b*, 12*c*) held by the needle holder (12) are situated into the guide rails (11*a*, 11*b*) extending towards the side of the capsule chamber (11) (FIG. 12). When the press button (9) is actuated in order to pierce the capsule in the capsule chamber (11), the needles (12*b*, 12*c*) enter the capsule chamber (11) by moving through the guide rails (11*a*, 11*b*) and pierce the capsule in the capsule chamber (11).

Two needles (12*b*, 12*c*) are held by the needle holder (12) in order to pierce the capsule. When the press button (9) is pressed in order to pierce the capsule, the upper needle (12*b*) moves through the upper guide rail (11*a*), the lower needle (12*c*) moves through the lower guide rail (11*b*) upon the movement of the needle holder (12) towards the capsule chamber (11) and they pierce the capsule in the capsule chamber (11). The needles (12*b*, 12*c*) revert back to their first position after piercing the capsule and this is provided by means of a spring (13) (FIG. 12). This spring (13) is situated between the capsule chamber (11) and the needle holder (12). A connection rod (11*c*) reaching towards the hole (12*a*) in the centre of the needle holder (12) from the side of the capsule chamber (11) passes through this spring (FIG. 12).

Upon pressing the press button (9), while the needle holder (12) moves towards the capsule chamber, the connection rod (11*c*) moves through the hole (12*a*) in the centre of the needle holder and the spring (13) is compressed. In the case that the press button (9) is released while the spring (13) reverts back to its previous position, the needle holder (12) and therefore the needles (12*b*, 12*c*) revert back to their first position.

Figure 5B:
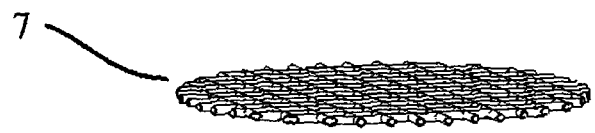
FIG. 5b is a perspective view of the filter.

An air intake duct (5) is inserted into the mouthpiece (2) in order to provide the delivery of the medicament in dry powder form comprised in the capsule to the patient during inhalation (FIG. 12). One end of this air intake duct (5) reaches to the inlet of the mouthpiece (2); the other end goes into the filter connector (6). According to this, thanks to the fact that the filter connector (6) is connected both to the interlocking points (2*b*, 2*c*) on the side part of the mouthpiece (2) and the air intake duct (5) inserted into the mouthpiece (2), it is fixed to the mouthpiece (2). During inhalation, the filter (7) showed in FIG. 5*b* and providing the medicament in dry powder form comprised in the capsule to be sieved is held by the filter connector (6) showed in FIG. 5*a*. According to this, the medicament in dry powder form in the capsule pierced is delivered to the patient by means of the mouthpiece after passing through the filter (7), the filter connector (6) and the air intake duct (5).

After the capsule in the capsule chamber (11) is pierced, the medicament in dry powder form comprised in the capsule becomes ready for inhalation. When the safety lock button (8) is pressed in order to reactuate it after the inhalation of the medicament in dry powder form, the front extension (6*c*) of the filter connector is detached from the left locking latch (8*b*) of the safety lock button and released. In this position, the mouthpiece (2) can be rotated away from the mid-plate (3) again and the empty capsule in the capsule chamber (11) can be removed (FIG. 8).

After the capsule in the capsule chamber (11) is removed, if it is required to clean the bottom-casing (4) of the device, the mid-plate (3) can be rotated around the hinge (10) away from the bottom-casing by holding the holding member (3*b*) situated on the mid-plate and by this way the bottom-casing (4) can be cleaned easily.

While using the device, the mouthpiece cover (1) and the mouthpiece (2) which are released simultaneously when the safety lock button (8) is actuated are rotated together away from the mid-plate (3) in order to load a capsule into the capsule chamber (11) before inhalation. After the mouthpiece (2) and the mouthpiece cover (1) are rotated together by 90°, the mouthpiece (2) stops at 90° and the mouthpiece cover (1) and the mouthpiece (2) are separated from each other as the mouthpiece cover (1) continues to rotate. After the capsule is loaded to the capsule chamber (11), the mouthpiece (2) is rotated over the mid-plate (3) again and the position of the mouthpiece (2) is fixed by interlocking the left locking latch (8*b*) on the safety lock button (8) to the hole of the front extension (6*c*) belonging to the filter connector which is internally interlocked to the mouthpiece. After the position of the mouthpiece (2) is fixed, the press button (9) which is situated independent from the safety lock button (8) is actuated when the patient presses on it. The needle holder (12) which is in contact with the press button (9) is pushed towards the capsule chamber (11) as the press button (9) is actuated. While the needle holder (12) is pushed towards the capsule chamber (11) by press button (9) in order to pierce the capsule in the capsule chamber (11), the spring (13) between the capsule chamber (11) and needle holder (12) is compressed, the needles (12*b*, 12*c*) carried by the needle holder (12) move through the guide rails (11*a*, 11*b*) extending towards the side of the capsule chamber (11) and the capsule in the capsule chamber (11) are pierced by these needles (12*b*, 12*c*). After the capsule is pierced by the needles (12*b*, 12*c*), while the spring (13) reverts back to its old position, the needles (12*b*, 12*c*) also revert back to their first positions as the press button is released. The dry powder formulation comprised in the capsule becomes ready for inhalation.

During inhalation, after the medicament in dry powder form in the pierced capsule exits the capsule chamber (11), it is delivered to the patient by means of the mouthpiece (2) after passing through the filter (7), filter connector (6) and air intake duct (5).

The inhalation device of the present invention comprising capsule can be made of the same or different materials. According to this, each component of the inhalation device can be made of any suitable material, though it is preferably selected from a group comprising styrene, acrylonitrile, polyoxymethylene, acrylic polymethyl methacrylate, cellulose acetate, polyetheretherketone, polyvinyl chloride, polyethylene, polypropylene, acrylonitrile butadiene styrene, silicon, polycarbonate, polyamide, polystyrene, polyurethane or fluoropolymer types. In addition, each component of the device can be in any suitable color.

The capsule used in the inhalation device comprising capsules according to the present invention can be made of any suitable component, though it is preferably made of a material selected from a group comprising gelatin, chitosan, starch and/or starch derivatives, cellulose and/or cellulose derivatives or synthetic polymers. In addition, the capsule of the present invention is composed of intertwining top and bottom parts. The top and the bottom parts of said capsule can be made of identical or different materials.

According to this, in the case that the capsule used in the present invention is made of cellulose or its derivatives, the capsule material can be selected from, but not limited to, a group comprising hydroxypropyl cellulose, hydroxypropylmethyl cellulose, methyl cellulose, hydroxymethyl cellulose, hydroxyethyl cellulose.

In the case that the capsule that shall be used in the present invention is synthetic polymer, the capsule material can be selected from, but not limited to, a group comprising polyethylene, polyester, polyetheleneteraphtalate, polycarbonate or polypropylene.

In the case that the capsule material that shall be used in the present invention is gelatin, additional agents having different molecular weights such as polyethylene glycol, sorbitol, glycerol, propylene glycol, polyethylene oxide-polypropylene oxide block copolymers and/or other polyalcohols and polyethers can be used.

In addition, the capsule which is used in the inhalation device of the present invention and wherein the medicament in dry powder form is carried can be in any suitable form and color on the condition that the medicament has the above-mentioned characteristic features.

The capsule wherein the medicament in dry powder form is carried in the inhalation device of the present invention which is illustrated in the drawings elucidated above is produced according to the prior art. According to the invention, the particle sizes of the active agents comprised in the medicament in dry powder form contained in the capsule are less than 10 μm, preferably less than 5 μm.

The inhalation device of the present invention has been designed so as to administer the medicament in dry powder form used in monotherapy or combined therapy. The term "monotherapy" refers to inhalation treatment wherein the medicament in dry powder form comprising a single active agent is used whereas the term "combined therapy" refers to inhalation treatment wherein the medicament in dry powder form comprising more than one active agent is used.

The medicament in dry powder form administered by means of the device of the present invention comprises at least one excipient in addition to the active agent or agents. These excipients are generally chosen from a group comprising monosaccharides (glucose, arabinose, etc.), disaccharides (lactose, saccharose, maltose, etc.), oligo- and polysaccharides (dextran, etc.), polyalcohols (sorbite, mannite, xylite), salts (sodium chloride, calcium carbonate, etc.) or combinations thereof According to the present invention, the medicament in dry powder form preferably comprises lactose as the excipient. The medicament in dry powder form comprises fine or coarse excipient particles preferably having various particle size ranges in order to transmit the required amount to the lungs.

The active agent or active agents comprised in the dry powder medicament which is stored in capsules used in the device according to the present invention can be selected from a group comprising cromolyns, anti-infectives, antihistamines, steroids, antiinflammatories, bronchodilators, leukotirene inhibitors, PDE IV inhibitors, antitussives, diuretics, anticholinergics, hormones, xanthines and pharmaceutically acceptable derivatives thereof The active agent comprised in the medicament in dry powder form delivered via the inhalation device according to the present invention is preferably selected from a group comprising tiotropium, oxitropium, flutropium, ipratropium, glicopironium, flunisolid, beclomethasone, budesonide, fluticasone, mometasone, ciclesonide, rofleponide, dexamethasone, montelukast, methylcyclopropane acetic acid, sodium cromoglicat, nedocromil sodium, enprofylline, theophylline, roflumilast, ariflo (cilomilast), salmeterol, salbutamol, formoterol, terbutaline, carmoterol, indacaterol, cetirizine, levocetirizine, efletirizine, fexofenadine and racemates, free base, enantiomers or diastereomers and pharmaceutically acceptable salts, solvates and/or hydrates or a combination thereof.

The device according to the present invention is used in administration of the medicament in dry powder form which is used in treatment of many respiratory diseases, particularly in asthma, chronic obstructive pulmonary disease (COPD) and allergic rhinitis. Accordingly, the respiratory tract diseases comprise, but not limited to, allergic or non-allergic asthma at any phases, acute lung injury (ALI), acute respiratory distress syndrome (ARDS), exacerbation of airways hyperactivity, bronchiectasis, chronic obstructive pulmonary including emphysema and chronic bronchitis, airways or lung diseases (COPD, COAD or COLD), pneumoconiosis, aluminosis, anthracosis, asbestosis, chalicosis, ptilosis, siderosis, silicosis, tabacosis and byssinosis. The device of the present invention can be used in prophylactic or symptomatic treatment. In addition, the medicament in dry powder form which is preferably used in the symptomatic treatment of allergic asthma and COPD is administered to the patient via the device of the present invention.

The invetion claimed is:

1. An inhalation device for inhalation of a medicament in dry powder form from capsules, the device comprising:
    a bottom-casing (4),
    a mid-plate (3) covering the bottom-casing (4),
    a capsule chamber (11) integrated with the mid-plate to place the capsule,
    a filter (7) to filter the medicament in dry powder form,
    a filter connector (6) to hold the filter (7),
    a mouthpiece (2) that closes over the mid-plate (3)and into which the filter connector (6) is inserted,
    a mouthpiece cover (1) to cover the mouthpiece (2),
    a hinge (10) providing a connection between the mouthpiece cover (1), the mouthpiece (2), the mid-plate (3) and the bottom-casing (4),
    at least one needle (12b, 12c) to pierce the capsule in the capsule chamber (11),
    a movable press button (9) to push the at least one needle (12b, 12c) into the capsule chamber (11),
    a safety lock button (8) to prevent movement of the mouthpiece (2) and the mouthpiece cover (1) when the inhalation device is in sleep mode, and
    locking latches (8a, 8b) situated on an upper side of the safety lock button (8) that interlock with holes of extensions (6c, 6d, 1b, 1c) belonging to the filter connector (6) and mouthpiece cover (1), wherein:
    the safety lock button (8) is connected with both the filter connector (6) inserted into the mouthpiece (2) and the mouthpiece cover (1) and wherein
    when the safety lock button (8) is in actuation position, the locking latches (8a, 8b) detach from the extensions (6c, 6d, 1b, 1c) and both the mouthpiece cover (1) and the mouthpiece (2) are released simultaneously.

2. The inhalation device according to the claim 1, wherein the connection among the safety lock button (8), the filter connector (6), and the mouthpiece cover (1) is enabled by interlocking of the extensions (6c, 6d, 1b, 16c) situated on the filter connector and the mouthpiece cover to the locking latches (8a, 8b) situated on the upper side of the safety lock button.

3. The inhalation device according to the claim 2, wherein the extensions (6c, 6d, 1b, 1c) of the filter connector (6) and the mouthpiece cover (1) are respectively situated under the mouthpiece (2) and the mouthpiece cover (1), wherein when the mouthpiece and the mouthpiece cover are closed, the extensions are inserted into the bottom-casing (4).

4. The inhalation device according to claim 1, wherein the locking latch (8*a*) is interlocked to the extension (1*b*) under the mouthpiece cover (1) while the locking latch (8*b*) is interlocked to the extension (6*c*) belonging to the filter connector when the safety lock button (8) is in sleep mode.

5. The inhalation device according to claim 1, wherein the device has nails (2*d*) that form on the exterior surface of the mouthpiece (2) as the filter connector (6) interlocks with the mouthpiece (2), and wherein the device comprises holes (1*d*, 1*e*) situated on the inner surface of the mouthpiece cover (2) into which the nails can insert.

6. The inhalation device according to claim 1, wherein the mouthpiece (2) comprises a hinge element (2*a*) situated on the side of the mouthpiece with a protruding structure that prevents the movement of the mouthpiece (2) more than 90°.

7. The inhalation device according to claim 1, wherein the mouthpiece cover (1) and the mouthpiece (2) can be rotated together by 90°.

8. The inhalation device according to claim 1, wherein the mouthpiece (2) can be rotated only by 90° and the mouthpiece cover (1) can be rotated by 180°.

9. The inhalation device according to claim 1, wherein the safety lock button (8) comprises a flexible part (8*c*) to move the safety lock button into the bottom-casing (4) when actuated and to revert back to its first position when released.

10. The inhalation device according to claim 1, wherein the press button (9) is configured to be actuated independently from the safety lock button (8).

11. The inhalation device according to claim 1, wherein the mouthpiece (2) comprises an air intake duct (5), one end of which reaches to an inlet of the mouthpiece (2) and the other end of which passes through the filter connector (6).

12. The inhalation device according to claim 1, wherein the medicament in dry powder form can be sieved through the filter (7) to enter into an air intake duct (5) without dispersing.

13. The inhalation device according to claim 1, wherein the capsule chamber (11) and the mid-plate (3) are adjacent to each other and the capsule chamber (11) is situated under the mid-plate (3).

14. The inhalation device according to claim 1, wherein said device comprises a capsule chamber (11) and guide rails (11*a*,11*b*) extending towards the side part of the capsule chamber (11) through which the at least one needle (12*b*, 12*c*) moves to pierce the capsule.

15. The inhalation device according to claim 1, wherein the at least one needle (12*b*, 12*c*) is held by a needle holder (12).

* * * * *

UNITED STATES PATENT AND TRADEMARK OFFICE
CERTIFICATE OF CORRECTION

PATENT NO. : 9,849,255 B2
APPLICATION NO. : 14/360014
DATED : December 26, 2017
INVENTOR(S) : Mahmut Bilgic It is certified that error appears in the above-identified patent and that said Letters Patent is hereby corrected as shown below:

In the Claims

Column 12, Line 26, replace "The invetion claimed is" with --The invention claimed is--;
    Line 35, in Claim 1, replace "mid-plate (3)and" with --mid-plate (3) and--;
    Line 62, in Claim 2, replace "(6c, 6d, 1b, 16c)" with --(6c, 6d, 1b, 1c)--.

Column 13, Lines 19-20, in Claim 6, replace "90° ." with --90°.--;
    Line 25, in Claim 8, replace "180° ." with --180°.--.

Signed and Sealed this
Fourth Day of June, 2019

Andrei Iancu
*Director of the United States Patent and Trademark Office*